United States Patent [19]
Schiel et al.

[11] Patent Number: 5,993,213
[45] Date of Patent: Nov. 30, 1999

[54] SUPERSTRUCTURE FOR AN ENDOSTEAL DENTAL IMPLANT

[75] Inventors: Harald Schiel, Baiergasse 41A, CH-4126 Bettingen; Rolf Frischherz, Langenthal; Martin Messerli, Bettlach, all of Switzerland

[73] Assignee: Harald Schiel, Bettingen, Switzerland

[21] Appl. No.: 08/875,155

[22] PCT Filed: Nov. 20, 1995

[86] PCT No.: PCT/CH95/00273

§ 371 Date: Nov. 21, 1997

§ 102(e) Date: Nov. 21, 1997

[87] PCT Pub. No.: WO97/18771

PCT Pub. Date: May 29, 1997

[51] Int. Cl.$^6$ ................................ A61C 3/00; A61C 8/00
[52] U.S. Cl. ................................................ 433/173; 433/24
[58] Field of Search ................................... 433/8, 23, 24, 433/172, 173, 174, 180

[56] References Cited

U.S. PATENT DOCUMENTS

| | | |
|---|---|---|
| 4,604,057 | 8/1986 | Viglietti ........................... 433/9 |
| 4,988,292 | 1/1991 | Rosen ............................. 433/8 |
| 5,066,224 | 11/1991 | Block et al. ..................... 433/7 |
| 5,071,345 | 12/1991 | Rosen ............................. 433/17 |
| 5,082,442 | 1/1992 | Rosen ............................. 433/17 |
| 5,205,746 | 4/1993 | Chanavaz ........................ 433/174 |
| 5,232,364 | 8/1993 | Rosen ............................. 433/133 |
| 5,564,924 | 10/1996 | Kwan ............................. 433/173 |
| 5,697,779 | 12/1997 | Sachdeva et al. ............... 433/24 |
| 5,769,630 | 6/1998 | Hoffman ......................... 433/24 |
| 5,836,768 | 11/1998 | Hüskens et al. ................. 433/173 |

FOREIGN PATENT DOCUMENTS

| | | |
|---|---|---|
| WO94/14388 | 7/1994 | WIPO ........................... 433/174 |
| WO96/19946 | 7/1996 | WIPO . |

*Primary Examiner*—Ralph A. Lewis
*Attorney, Agent, or Firm*—Walter C. Farley

[57] ABSTRACT

A superstructure (1) for an endosteal dental implant (2) has a longitudinal axis (11) and an outer surface (12), which has buccal, lingual, mesial and distal regions, and an annular surface (8) which is intended for the connection to a dental implant (2) and is orthogonal to the longitudinal axis (11). The superstructure (1) is further provided with a connection for accommodating an orthodontic element (6).

10 Claims, 1 Drawing Sheet

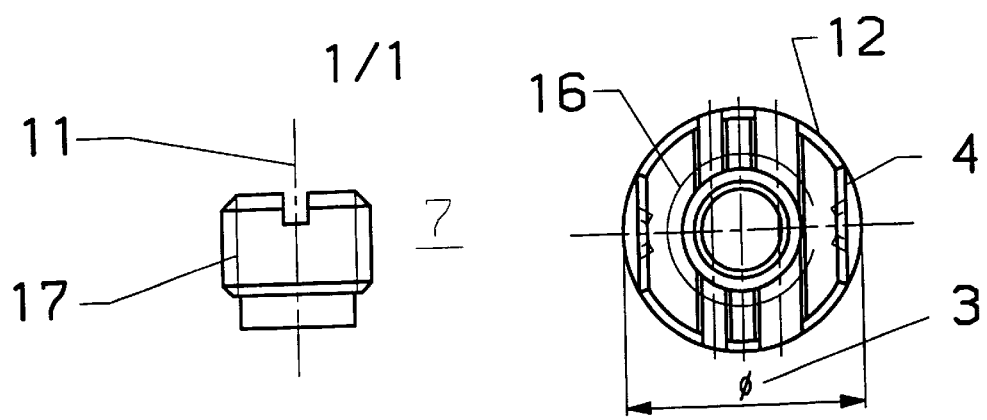
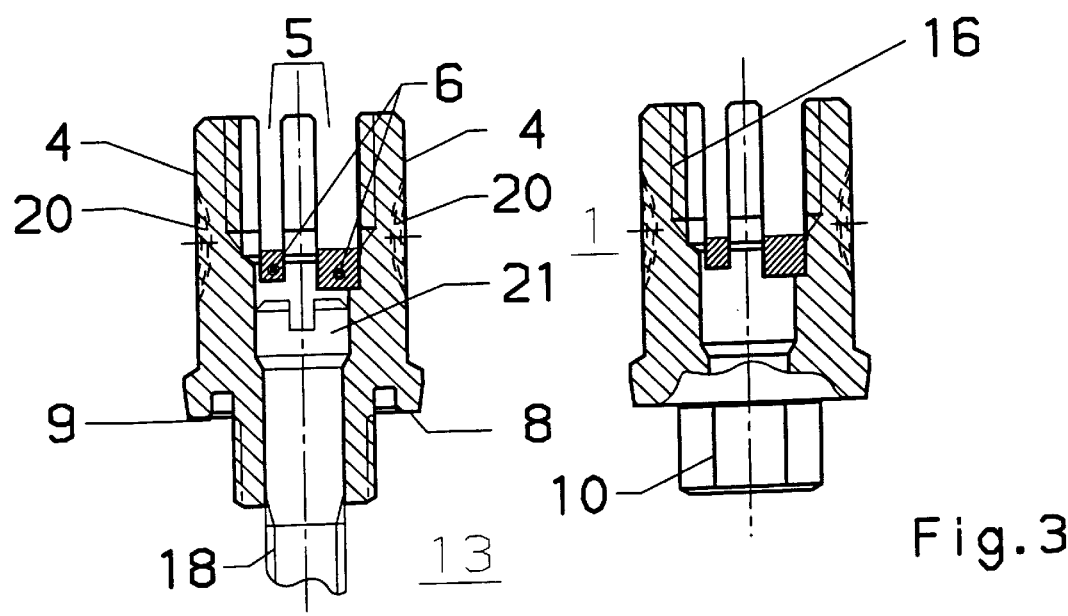
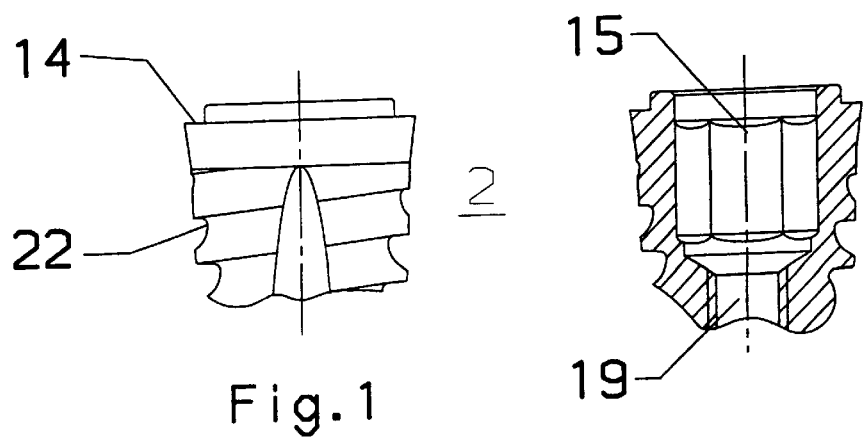

SUPERSTRUCTURE FOR AN ENDOSTEAL DENTAL IMPLANT

FIELD OF THE INVENTION

The invention relates to a superstructure for an endosteal dental implant as well as an orthodontic device with such a superstructure mounted on a dental implant.

BACKGROUND OF THE INVENTION

The amount of orthodontic treatments of adults and adolescents to correct the dental position is increasing. So far the corrections of the dental position have been undertaken partially by means of a head-gear through which the forces on the bows and clasps which lie close to the teeth may be applied. The head-gear will act on the rows of the teeth about 8 hours as a general rule. The head-gear is therefore only intermittently effective and is felt by the bearer as extremely cumbersome.

SUMMARY OF THE INVENTION

An object of the invention is to produce a superstructure for an endosteal dental implant which serves as an anchorage for the introduction of the forces in orthodontic corrections.

The advantages achieved by the invention are basically as follows:

No head-gear has to be applied what represents a considerable improvement of the comfort;

The translation force (anchorage) is not only intermittently effective but permanent for 24 hours; and As the superstructure may be attached as an anchorage at any arbitrary anatomical position where a dental implant may be fixed the orthodontic wires may be attached not only at the outer sides of the teeth (buccal) but also at the inner sides of the teeth (lingual).

This offers advantages of esthetics which are to be rated high above all else in the treatment of adults.

BRIEF DESCRIPTION OF THE DRAWINGS

The invention and embodiments of the invention are discussed in more detail in the following with reference to the accompanying schematic drawings thereof wherein:

FIG. 1 is an exploded side elevation in a longitudinal section through the orthodontic device according to the invention;

FIG. 2 is a top plan view of the superstructure of the orthodontic device according to FIG. 1;

FIG. 3 is a sectional side elevation of the superstructure of the orthodontic device according to FIG. 1; and FIG. 4 is a longitudinal section through the dental implant of the orthodontic device according to FIG. 1.

DESCRIPTION OF PREFERRED EMBODIMENTS

The orthodontic device illustrated in FIG. 1 basically consists of a superstructure mounted on an endosteal dental implant 2 in which (as shown in FIG. 1) an orthodontic element 6 e.g. a wire is either attached with a screw 7 or is adherable without the screw at its area 4.

For better orientation some geometrical elements of the superstructure are defined in the following:

A) a longitudinal axis 11 coaxial to the dental implant 2;

B) an outer surface area 12 having buccal, lingual, mesial and distal areas; and C) an annular shoulder 8 orthogonal to the longitudinal axis 11 suitably position for connection to the dental implant 2.

In the buccal and lingual area of the surface area 12 areas 4 are provided which extend parallel to the longitudinal axis 11 and are flattened opposite the maximum outer diameter 3 on which orthodontic brackets (particularly adhesive-brackets) or square bows are attachable. For this purpose the areas 4 are preferably planar polished and roughened. The roughness $R_a$ of the area 4 lies preferably in the range of from 3.3 to 12.5 $\mu$m. Additionally retentions 20 preferably with the shape of grooves can be inserted in the area 4.

The superstructure 1 further provides passing slots 5 running from the mesial to the distal area of the surface area 12 wherein orthodontic wires 6 can be inserted from above and be radially and axially fixed by means of the screw 7. Instead of the screw 7 naturally other known fixation systems e.g. bayonet joints or glued joints can be employed.

In case of the employment of a screw 7 the superstructure 1 has coaxial to the longitudinal axis 11 an internal thread 16 whereto the screw 7 which is provided with a corresponding external thread 17 is insertable.

To ensure a rotation stable junction of the superstructure 1 with the endosteal dental implant 2 the superstructure 1 possesses—as shown in FIG. 3 and 4—a hexagonal insert piece 10 which fits in a corresponding hexagon socket 15 of the dental implant 2. The junction between the superstructure 1 and the dental implant 2 ensues by means of a fixation screw 13 which is insertable from above into the interior of the superstructure 1 and is screwable by means of its external thread 18 into a corresponding internal thread 19 of the dental implant 19.

Therefore, the geometry of the junction is preferably shaped such that the annular area 8 of the superstructure 1 has a small gap 9 of about 5 $\mu$m corresponding to the annular area 14 of the dental implant 2, which minimizes the penetration of bacteria.

The depth of the slots 5 measured from above reaches maximally to the head 21 of the fixation screw 13. As shown in FIG. 1 two slots 5 for different strong wires 6 are provided and the free depths of the slots 5 are chosen to be equally as large as wires 6 which means that for the wider slot which has to contain a wider wire the depth is to be chosen accordingly larger.

The dental implant 2 will be brought in at a toothless place of the teeth bow or rather palantial into the bone.

We claim:

1. A superstructure (1) for an endosteal dental implant (2) comprising a body having a top, a bottom, a longitudinal axis (11) extending through said top, an outer surface area (12) having buccal, lingual, mesial and distal regions, and an annular means (8) at said bottom orthogonal to said longitudinal axis (11) for connection to a dental implant;

an hexagonal insert piece (10) at said bottom for providing a rotationally stable connection with an hexagonal socket of a dental implant; and means in said body defining at least one slot extending through said body from said mesial to said distal region, said at least one slot opening upwardly toward said top of said superstructure and being dimensioned to receive an orthodontic wire (6).

2. A superstructure according to claim 1 including a dental implant on which said superstructure is mounted and wherein said annular area (8) has a gap of 4–6 μm to an annular area (14) of said dental implant.

3. A superstructure according to claim 1 comprising
means comprising a planar area (4) in at least one of said buccal and lingual regions of said outer surface area, each said planar area being flattened relative to a maximal outer diameter and extending parallel to said longitudinal axis (11) for receiving brackets for the attachment of an orthodontic device.

4. A superstructure according to claim 3 wherein said planar area is roughened.

5. A superstructure according to claim 3 wherein each said planar area comprises grooves (20) for retaining said brackets.

6. A superstructure (1) for an endosteal dental implant (2) comprising
a body having a top, a bottom, a longitudinal axis (11) extending through said top, an outer surface area (12) having buccal, lingual, mesial and distal regions, and an annular means (8) at said bottom orthogonal to said longitudinal axis (11) for connection to a dental implant;
an internal thread adjacent the top of said body coaxial with said longitudinal axis;
a screw (7) having an external thread threadedly matable with said internal thread for radially and axially guiding an orthodontic element inserted into said at least one slot; and
means in said body defining at least one slot extending through said body from said mesial to said distal region, said at least one slot opening upwardly toward said top of said superstructure and being dimensioned to receive an orthodontic wire (6).

7. A superstructure according to claim 6 including a dental implant on which said superstructure is mounted and wherein said annular area (8) has a gap of 4–6 μm to an annular area (14) of said dental implant.

8. A superstructure according to claim 6 comprising
means comprising a planar area (4) in at least one of said buccal and lingual regions of said outer surface area, each said planar area being flattened relative to a maximal outer diameter and extending parallel to said longitudinal axis (11) for receiving brackets for the attachment of an orthodontic device.

9. A superstructure according to claim 8 wherein said planar area is roughened.

10. A superstructure according to claim 8 wherein each said planar area comprises grooves (20) for retaining said brackets.

* * * * *